US008506570B2

(12) United States Patent
Colquhoun et al.

(10) Patent No.: US 8,506,570 B2
(45) Date of Patent: Aug. 13, 2013

(54) BURR GUIDE ASSEMBLY

(75) Inventors: Callum Colquhoun, Belgrave (AU); Michael Rock, Leeds (GB); David Paul Thomas, Wakefield (GB)

(73) Assignee: Depuy International Limited (GB)

( * ) Notice: Subject to any disclaimer, the term of this patent is extended or adjusted under 35 U.S.C. 154(b) by 1595 days.

(21) Appl. No.: 11/754,925

(22) Filed: May 29, 2007

(65) Prior Publication Data
US 2008/0015608 A1  Jan. 17, 2008

(51) Int. Cl.
*A61B 17/17* (2006.01)
(52) U.S. Cl.
USPC ............................................. 606/87; 606/79
(58) Field of Classification Search
USPC ............. 606/87–88, 96–98, 167–280, 79–80; 623/13.12, 13.19, 13.2, 18.11, 20.14–20.19, 623/20.2, 20.21–21.29, 20.3, 20.31–20.36, 623/23.39
See application file for complete search history.

(56) References Cited

U.S. PATENT DOCUMENTS

| | | | | |
|---|---|---|---|---|
| 4,574,794 A | * | 3/1986 | Cooke et al. | 606/88 |
| 5,171,244 A | * | 12/1992 | Caspari et al. | 606/88 |
| 5,207,680 A | * | 5/1993 | Dietz et al. | 606/86 R |
| 5,228,459 A | | 7/1993 | Caspari | |
| 5,342,367 A | * | 8/1994 | Ferrante et al. | 606/86 R |
| 5,454,816 A | * | 10/1995 | Ashby | 606/88 |
| 5,653,714 A | * | 8/1997 | Dietz et al. | 606/87 |
| 5,683,397 A | * | 11/1997 | Vendrely et al. | 606/88 |
| 6,419,428 B2 | * | 7/2002 | Ajimi et al. | 409/179 |
| 2003/0171756 A1 | | 9/2003 | Fallin | |
| 2004/0039394 A1 | | 2/2004 | Conti | |
| 2006/0052791 A1 | * | 3/2006 | Hagen et al. | 606/86 |
| 2006/0200163 A1 | * | 9/2006 | Roger et al. | 606/89 |

FOREIGN PATENT DOCUMENTS

| | | |
|---|---|---|
| DE | 10309987 | 9/2004 |
| DE | 10309987 A1 | 9/2004 |
| EP | 263292 | 4/1988 |
| EP | 263292 A1 | 4/1988 |
| EP | 1329198 | 7/2003 |
| WO | WO 03/070111 | 8/2003 |
| WO | WO 03070111 A2 | 8/2003 |
| WO | WO 2004/075763 | 9/2004 |
| WO | WO 2004075763 A1 | 9/2004 |

OTHER PUBLICATIONS

PCT Written Opinion, 7 pages.
International Search Report, dated Oct. 21, 2005, 5 pages.

(Continued)

*Primary Examiner* — Nicholas Woodall
*Assistant Examiner* — Larry E Waggle, Jr.

(57) ABSTRACT

A burr guide assembly is described for guiding a burr tool during a procedure wherein the burr tool is used to cut a bone. The guide assembly includes a housing which is configured to be attached to the bone, a guide sleeve attached to the housing such that the guide sleeve can freely pivot about a pivot axis within a defined range, and a burr tool. The guide sleeve has a bore that extends along its length, which is located eccentrically within the guide sleeve. The burr tool has a cutting portion that is configured to be at least partially disposed within the bore. The guide sleeve is mounted within the housing such that the cutting portion is substantially restricted to movement in a plane that is perpendicular to the pivot axis.

11 Claims, 12 Drawing Sheets

(56) References Cited

OTHER PUBLICATIONS

Hagen T; Reich J: German Patent No. DE 10309987A1; Sep. 16, 2004; English Abstract; Dialog® File No. 351 Accession No. 14462007; Derwent World Patents Index; © 2009 Derwent Information Ltd. All rights reserved.

Bider K; Frey O: European Patent No. EP 263292A; Apr. 13, 1988; English Abstract; Dialog® File No. 351 Accession No. 4366170; Derwent World Patents Index; © 2009 Derwent Information Ltd. All rights reserved.

Boettiger R, et al.; PCT International Patent No. WO 2003070111A2; Aug. 28, 2003; English Abstract; Dialog® File No. 351 Accession No. 13543428; Derwent World Patents Index; © 2009 Derwent Information Ltd. All rights reserved.

* cited by examiner

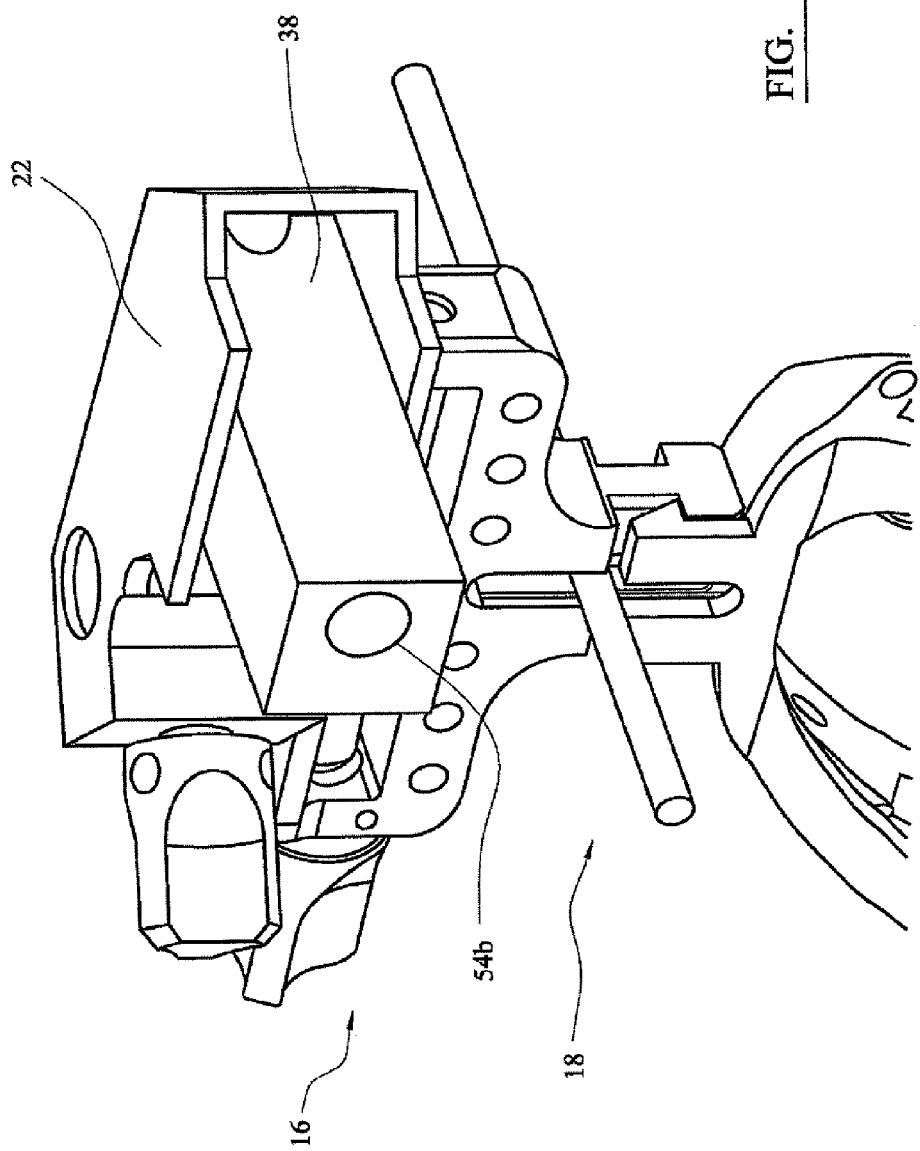

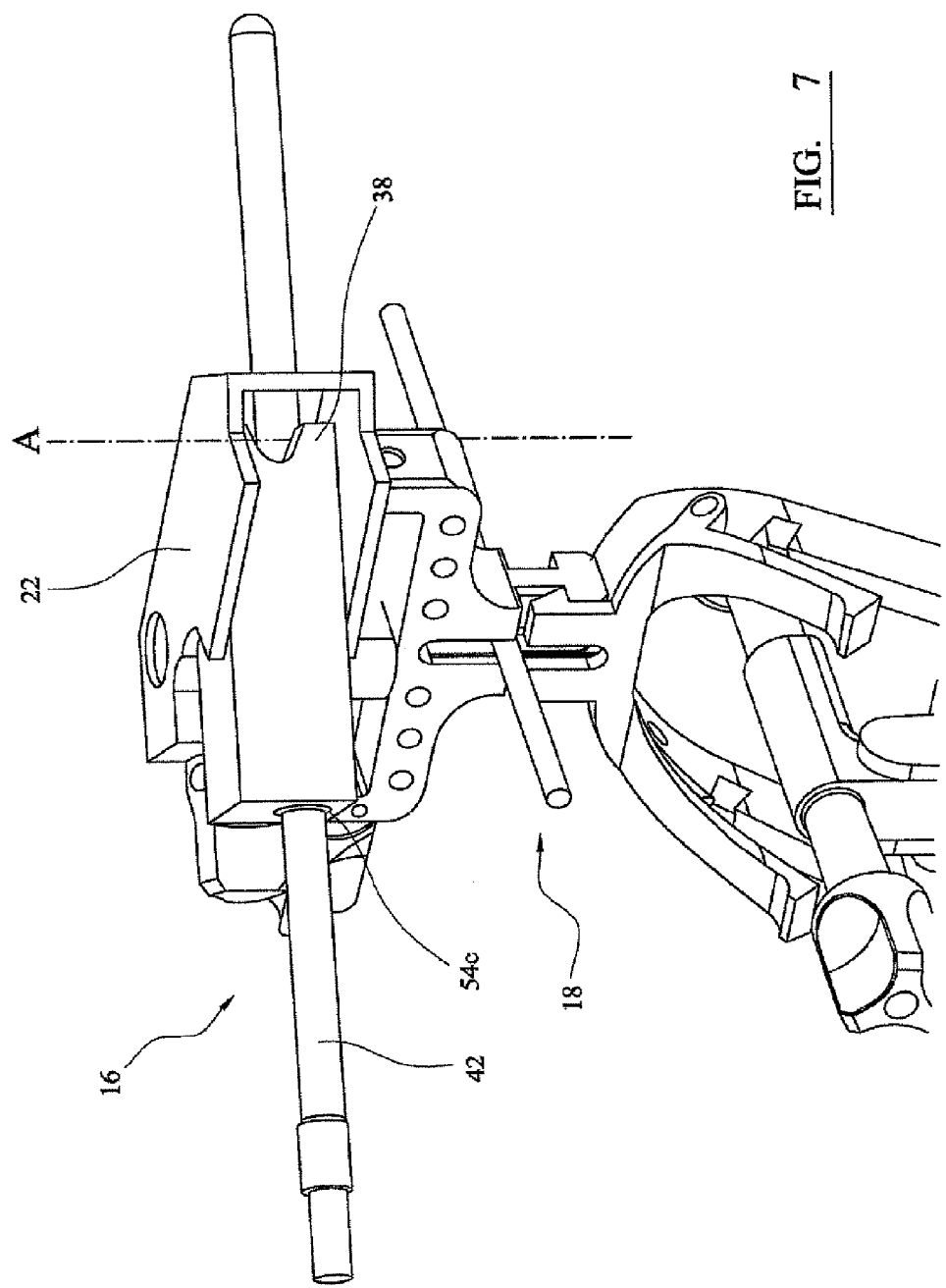

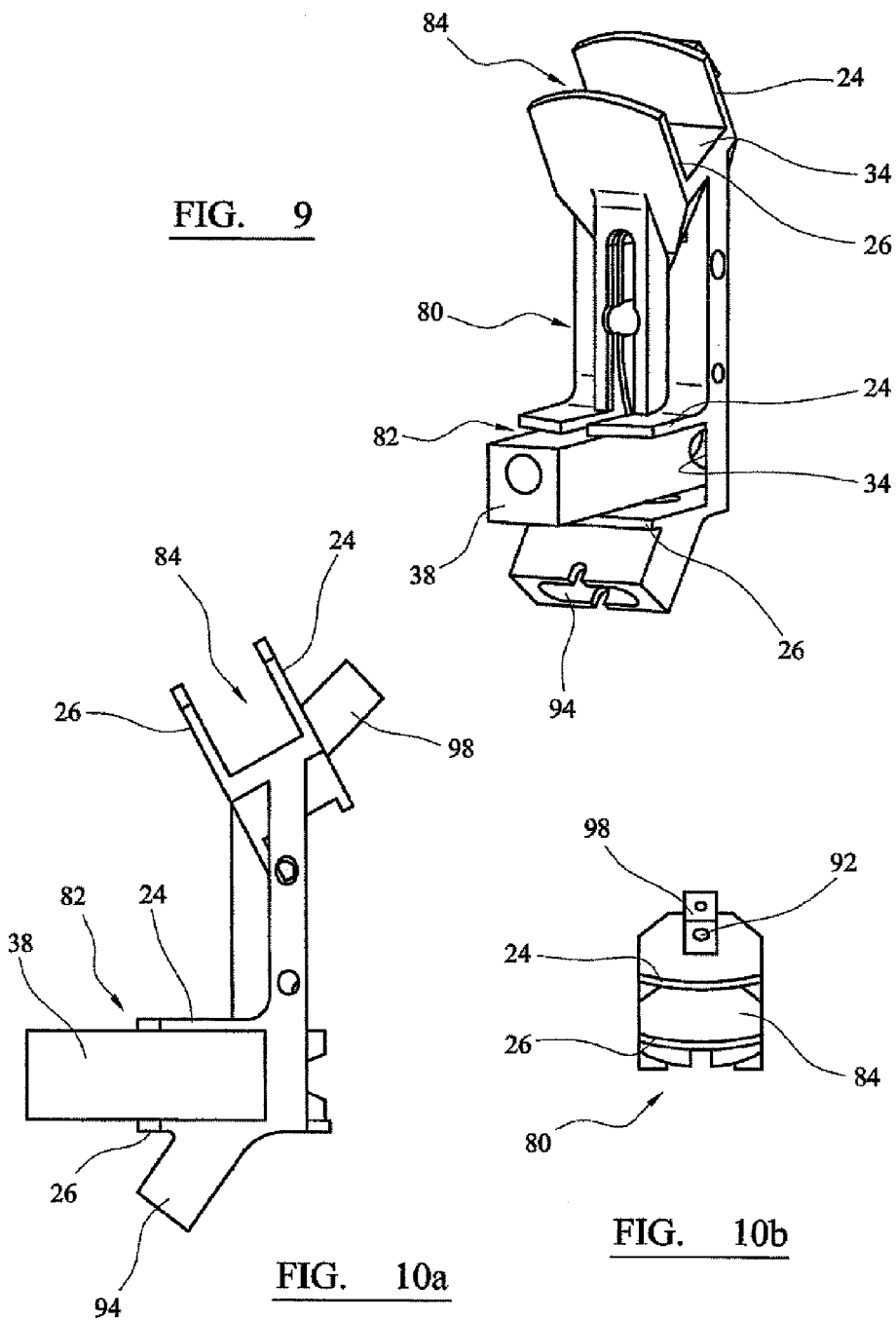

BURR GUIDE ASSEMBLY

This invention relates to a burr guide assembly for guiding a burr tool in a plane to resect a bone.

In order to prepare a bone for a component of an orthopaedic joint prosthesis, it can be necessary to provide at least one planar surface on the bone. The planar surface can be provided by resecting the bone. The bone can be resected using a cutting instrument, such as a saw or a burr tool which is inserted through an incision which provides access to the bone. It can be desirable to minimise the size of the incision, especially in order to reduce the period taken for the patient to recover from the surgery. The size of a cutting instrument can determine the minimum size of the incision.

It can also be important to be able to control the location and dimensions of the resection accurately. This is because the bone needs to be appropriately shaped and sized in order to receive the prosthesis. Incorrectly located or sized resections can reduce the quality of the fit of component of the joint prosthesis on the bone. If the component of the joint prosthesis is not fitted correctly, then the effectiveness of the prosthetic joint might be reduced. Also, an incorrectly fitted component of prosthesis may cause excessive wear of the prosthetic joint and/or the bone, causing discomfort to the patient, and decreasing the lifetime of the prosthetic joint.

Further, it can be important to minimise the damage to tissue surrounding the bone that is to be resected. Any unwanted damage to surrounding tissue can be caused by the cutting instrument inadvertently contacting the tissue during resection.

The present invention provides a burr guide assembly which comprises a burr guide sleeve and a housing in which the burr guide sleeve is mounted so that the sleeve can pivot about its mounting, to control the path of the burr tool when resecting the bone.

Accordingly, in one aspect, the invention provides A burr guide assembly for guiding a burr tool during a procedure in which the burr tool is used to cut a bone, which comprises: a housing which can be fastened to the bone; a guide sleeve which is pivotally mounted in the housing, having a bore extending along its length in which a burr tool can be received such that the cutting portion of the burr tool extends from the sleeve towards the bone which is to be cut, in which the bore is located eccentrically within the guide sleeve, and in which the sleeve is mounted in the housing for pivotal movement around an axis so that the cutting portion of the burr tool is restricted to movement in a plane which is perpendicular to that axis; and a burr tool which is a sliding fit in the guide sleeve.

It is an advantage of the present invention that the path the burr tool will take during resection of the bone can be determined before the resection procedure. Inaccuracies in the resection caused by human error, or due to difficulties experienced by the surgeon during the resection procedure, can be reduced by the present invention. As the path the burr tool can take is fixed, the surgeon cannot accidentally deviate from the desired path. Also, any translational force on the burr tool caused by the cutting action of the burr tool on the bone, which might tend to cause the burr to deviate from the desired path, will be counteracted by the sleeve.

Preferably, the burr tool includes a drive unit for imparting a rotational force on it. The burr tool comprises a shaft that can be driven by the drive unit, wherein the shaft has cutting portion which has cutting teeth on its circumferential surface. Preferably, the cutting portion extends from the end of the shaft that is far from the end which can be fastened to the drive unit, towards its end close to the drive unit, along at least 25% of the length of the shaft, more preferably at least 30% of the length of the shaft, especially preferably at least 40% of the length of the shaft, for example, at least 50% of the length of the shaft.

The burr tool is restricted to movement in a plane. This is advantageous as it allows the use of a burr tool to achieve planar resection of a bone. It can be advantageous to use a burr tool instead of a saw to resect a bone, because a burr tool can require a smaller incision compared with a saw. There are particular advantages associated with minimising the size of the incision required, such as reducing patient discomfort and recovery time after the operation.

Preferably, the guide sleeve can be removed from the housing. There are particular advantages associated with being able to remove the guide sleeve from the housing. For example, this can aid in the cleaning of the assembly after it has been used. Further, when the guide sleeve can be removed from the housing, it can be possible to use different guide sleeves in the same housing. For example, guide sleeves having different sized bores can be used in the same housing. This allows the use of different sized burr tools to cut the bone in order to suit the particular requirements, including the size, shape or location of the cut. Further advantages can arise from the guide sleeve being removable from the housing as discussed below in relation to the guide sleeve having an eccentrically located bore.

The guide sleeve can be permanently mounted within the housing so that it cannot be subsequently removed. Although such an arrangement does not allow the use of different types of guide sleeve, this arrangement can be preferred when it is unlikely that the use of different sized burr tools will be used. Such arrangements can also be preferred due to the surgeon not having to be concerned with keeping the guide sleeve mounted within the housing when using the assembly. Guide sleeves can be permanently pivotally mounted within the housing through a number of standard bearing mechanisms. For example, two or more cylindrical recesses on the housing or on the guide sleeve can receive corresponding cylindrical protrusions on the other of the guide sleeve and the housing so that the guide sleeve pivots about the axis defined by the cylindrical protrusions.

When the guide sleeve is removable from the housing, the sleeve can have formations which interact with formations on the housing in order to allow the guide sleeve to pivot about an axis defined by the formations on the guide sleeve and housing. The formations can be provided by two pairs of cooperating protrusions and recesses. For example, the housing can have a protrusion which can be received within a recess on the guide sleeve. Preferably, the recesses are rounded, for example, semi-circular in shape. Therefore, the guide sleeve pivots about the axis defined by the cylindrical projections on the housing. Alternatively, a cylindrical projection can be provided towards the end of the guide sleeve which is close to the bone which is to be cut and a recess can be provided in the housing so that the cylindrical projection sits within the recess in the housing. The use of at least one cylindrical projection which interact with at least one recess allows the guide sleeve to be easily removed from the housing while still providing a firm and secure mechanism about which the guide sleeve can pivot. The recess can be open at one end to allow the projection to be slid into, and out of, it.

When the guide sleeve is removable from the housing, the guide sleeve can have formations which enable it to be mounted within the housing in at least two orientations, wherein the sleeve is pivotable about respective axes in each of the at least two orientations. Preferably, the guide sleeve can have formations which enable it to be mounted within the housing in at least three orientations, wherein the sleeve is pivotable about respective axes in each of the at least three orientations. For example, the guide sleeve can have formations on each of its sides which can engage with the formations on the housing of the assembly. This can enable the guide sleeve to be mounted in any one of four orientations in the housing.

This is advantageous because, when the guide sleeve is mounted in a first orientation, the bore can be positioned so that an axis defined by the length of the bore intersects an axis which extends perpendicularly to the intended cutting plane at a point which is farther from a point in the bone that lies on the axis which extends perpendicularly to the intended cutting plane, than the point at which the axis of the bore intersects the axis perpendicular to the intended cutting plane when the guide sleeve is mounted in the housing in a second orientation. Further, when the sleeve can be, and is mounted in a third orientation, the point at which the axis defined by the bore intersects the axis that extends perpendicularly to the intended cutting plane is at a point closer to a point in the bone that lies on the axis which extends perpendicularly to the intended cutting plane, than when in the second orientation. Therefore, when in use, the burr guide sleeve can be successively mounted in the first, second and third orientations to guide a burr tool in first, second and third planes to perform first, second and third cuts of the bone, wherein each cutting step removes a further portion of the bone.

The use of successive cutting steps can provide significant advantages. For example, it can be possible to use a single burr tool to remove a portion of bone that is thicker than the size of diameter of the burr tool. For example, it is possible to use a burr tool having a diameter of 2.5 mm to remove 7.5 mm from the surface of a bone, in three successive cutting steps. The burr tool guided in the first, second and third planes controlled by the guide sleeve mounted in the first, second and third orientations can each remove 2.5 mm from the surface of the bone. Therefore, in this example, in order to remove 7.5 mm from the surface of a bone, it is only necessary to make an incision in the patient through which a burr tool having a diameter of 2.5 mm can pass. Therefore, the use of successive cutting steps can allow the procedure to be performed through a smaller incision compared with a procedure in which a single cutting step is performed using a larger burr tool. This is particularly advantageous where very small incisions need to be made in the patient, for example, in minimal invasive surgery.

It can be preferable that the guide sleeve pivots about a common axis when it is mounted in each of the at least two orientations. In some circumstances, it can be preferable that the axis about which the guide sleeve pivots is different in each of the said orientations. For example, this can be preferable when it is necessary to provide at least two cuts in the bone that have different planes.

When the guide sleeve can be mounted in the housing in at least two orientations, it can be preferred for the axis defined by the bore to intersect the axis about which the guide sleeve pivots in at least one of its orientations. This can help to ensure that when the guide sleeve can be mounted in at least two orientations, the point at which the bore axis intersects an axis that extends perpendicular to the intended cutting plane is closer to a point in the bone that lies on the axis of the intended cutting plane, in one of the orientations than in the other orientation. Further, this ensures that when the guide sleeve can be mounted in at least three orientations, the difference in the distance between the point at which the bore axis intersects the axis of the intended cutting plane and the point in the bone that lies on the axis that extends perpendicular to the planar surface, is the same for the first and second orientations of the guide sleeve as it is for the second and third orientations of the guide sleeve (wherein, the first orientation is where the axis of the bore is farthest from the point in the bone, and the third orientation is closest to the point in the bone).

Preferably, the distance between the centre line of the bore and the centre line of the guide sleeve is not more than the transverse dimension of the bore. This can help ensure that as the sleeve is rotated from its first orientation to its second orientation, there is little or no gap left between the area defined by the bore in the first orientation and the area defined by the bore in the second orientation, in the direction parallel to the axis about which the sleeve pivots. Further, when the sleeve can be mounted within the housing in at least three orientations, there would be no gap left between the area that is defined by the bore in the second orientation and the area that is defined by the bore in the third orientation, in the direction parallel to the axis about which the sleeve pivots.

The distance between the centre line of the bore and the centre line of the guide sleeve can be less than the transverse dimension of the bore. This can help ensure that there is some overlap in the portion of bone that is defined by the bore of the burr guide sleeve when the guide sleeve is mounted in the first and second orientations. This can also help ensure that there is some overlap in the portion of bone that is defined by the bore of the burr guide sleeve when the guide sleeve is mounted in the second and third orientations.

Preferably, the distance between the centre of the bore and the centreline of the guide sleeve is not more than the radius of the bore. Preferably, the ratio of (i) the distance between the centre of the bore and the centreline of the guide sleeve to (ii) the radius of the bore, is not more than 0.8, more preferably not more than 0.7, for example, about 0.66.

Preferably, the sleeve has at least two pairs of opposite parallel walls. Preferably, the cross-sectional shape of the sleeve when viewed perpendicular to the axis of the guide sleeve is approximately rectangular, especially preferably square. This can be advantageous as when the guide sleeve is received within a housing having opposing parallel sides which are separated from each other by a distance slightly greater than the width of the sleeve, the sides of the guide sleeve will interact with the sides of the housing to oppose any twisting force imparted to the guide sleeve by the burr tool extending through the guide sleeve. Although the formations about which the guide sleeve pivots will oppose any rotational force imparted on the guide sleeve, the use of a rectangular or square cross-sectional sleeve within a close fitting housing can ensure that the rotational force is spread across the entire guide sleeve rather than at the point about which the guide sleeve pivots. This can help increase the strength and durability of the guide sleeve. It will be appreciated that other polygonal shapes can be used to achieve the same effect. For example the cross-sectional shape of the guide sleeve can be hexagonal or octagonal. Further, although there are advantages with providing a polygonal cross-sectional shape, the cross-sectional shape need not be polygonal. For example, the cross-sectional shape can be circular. In this case, the formations about which the guide sleeve pivots will oppose any rotational force imparted on the guide sleeve.

The guide sleeve defines a bore in which a burr tool can be received. The size of the bore should be sufficient for the burr tool to be a sliding fit, with minimum clearance which would allow play to reduce the accuracy of the location of the burr tool that is used to cut the bone. The guide sleeve can also be used to locate surgical instruments other than burr tools. For example, the sleeve can be used to locate drill bits. Preferably, the internal width of the bore is not less than 2 mm, more preferably, not less than 2.5 mm, especially preferably, not less than 3 mm. Preferably, the internal width of the bore is not more than 8 mm, more preferably not more than 6 mm, especially not more than 4 mm, for example, not more than 3 mm.

Preferably, the length of the guide sleeve is not less than 1 cm, more preferably not less than 2 cm, especially preferably not less than 3 cm, for example, not less than 4 cm. Preferably, the length of the guide sleeve is not more than 10 cm, more preferably not more than 8 cm, especially not more than 6 cm.

Preferably, the ratio of (i) the length of the guide sleeve to (ii) the distance between the end of the guide sleeve far from the bone and the point at which it is mounted within the housing is less than 4, more preferably less than 3, especially preferably less than 2. Most preferably, the guide sleeve is mounted at its end close to the bone (i.e. the ratio of (i) to (ii) is 1).

Preferably, the distance between the point about which the guide sleeve pivots and the surface of the bone is not more than 2 cm, more preferably not more than 2.5 cm, especially not more than 1 cm, for example, not more than 0.5 cm.

It is advantageous that the distance between the point at which the guide sleeve is mounted within the housing, and the surface of the bone to be cut, is minimised. This reduces the translational distance through which the axis, defined by the length of the guide sleeve, moves across the surface of bone for any given angle of rotation of the guide sleeve relative to the housing. This can enable the user of the assembly to have greater control over the movement of the burr tool in the plane when cutting the bone, because a greater translational movement of the cutting part of the burr tool far from the bone (i.e. at the point at which the user moves the burr tool) can be allowed relative to the translational movement of the burr tool close to the bone (i.e. at the point the burr tool cuts the bone). This in turn increases the accuracy by which the user of the assembly can cut the bone.

The guide sleeve is mounted within a housing which can be fastened either directly or indirectly to the bone. Preferably the housing is fastened indirectly to the bone by a jig instrument which can be fastened to a bone. Preferably, once fastened to the bone the jig can be adjusted so that the position of the mounting of the guide sleeve relative to the bone can be adjusted. Preferably, the position of the mounting can be adjusted in the medial/lateral, proximal/distal and posterior/anterior dimensions relative to the bone. Preferably, the rotational position of the mounting can be adjusted about x, y and z axes (i.e. three axes, each perpendicular to one another) relative to the bone. Preferably, the position of the mounting can be adjusted through the use of adjustment screws on the housing and/or the jig. However, any means for adjusting the position of the mounting can be used. Jig instruments can receive surgical instruments, cutting blocks or tools which can be fastened to the bone and subsequently adjusted so that the position of the tool or instrument can be accurately located relative to the bone are well known. Such jig instruments of this general kind are known, including those available from DePuy Products, Inc under the name CAS Preservation Tibial Jig (which is used as part of DePuy's MI TKR System surgical technique), and the ankle clamp based jig which forms part of the knee replacement instrument set under the trade mark Specialist 2. Preferably, the housing includes stops for limiting the angle through which the guide sleeve can pivot relative to the bone. Preferably, the stops limit the angle through which the guide sleeve can pivot to not more than 90 degrees, more preferably not more than 110 degrees, especially preferably not more than 130 degrees, and for example not more than 150 degrees. Preferably, the stops allow the guide sleeve to pivot through an angle of at least 45 degrees, more preferably at least 50 degrees, especially preferably at least 80 degrees, for example, at least 90 degrees.

Preferably, the housing provides at least two mountings in which a guide sleeve can be pivotally mounted. For example, when the guide sleeve can be removed from the housing, preferably each of the at least two mountings can receive the same guide sleeve. Preferably, the housing provides at least three mountings for the guide sleeve. Preferably, the mountings are configured such that when the guide sleeve is in use, the guide sleeve when mounted in each of the mountings can be used to guide a burr tool to provide a proximal/distal cut and a posterior chamfer and anterior chamfer in the bone. As will be understood, the mountings can also be configured such that when the guide sleeve is in use, the guide sleeve when mounted in one of the mountings can be used to guide a burr tool to provide a medial/lateral cut.

The housing can provide only two mountings in which the guide sleeve can be mounted in order to guide a burr tool to provide two of the cuts mentioned above. The housing can also provide a slot through which a burr tool can be inserted and which restricts the movement of the burr tool in one dimension so that movement of the burr in a second dimension can be allowed in order to provide one of the medial/lateral cut, proximal/distal cut or posterior and anterior chamfers.

When the burr guide sleeve is removable from the housing, the mounting in which the burr guide sleeve is pivotally mounted can also be used to fasten a drill guide block for determining the extremities of an area of bone to be removed in order to prepare the bone. Preferably, the assembly includes a drill guide block which can be fastened to the housing, and having an array of at least two closely spaced drill guide bores which define bone tissue which can be drilled by a drill bit extending through the bores towards the surface of the bone, in which the ratio of the distance between the centres of two adjacent ones of the bores to the diameter of each of those bores is not more than about 1.5. Details of such a drill guide block are disclosed in a co-pending application entitled A Drill Guide Assembly which is filed with the present application bearing agent's reference P211129. Subject matter that is disclosed in that application is incorporated in the specification of the present application by this reference.

The assembly can comprise a removable burr sheath that extends through the bore of the guide sleeve to protect tissue surrounding the bone from a burr tool extending through the bore. The sheath will protect the surrounding tissue from the rotating burr tool so as to prevent damage caused to the tissue by the burr tool. Preferably, the sheath is of a size that fits snugly within the bore so that the friction caused between the sheath and the bore prevents the sheath rotating within the bore during the burring procedure. Preferably, the internal width of the sheath is not less than 2 mm, more preferably, not less than 2.5 mm, especially preferably, not less than 3 mm. Preferably, the internal width of the sheath is not more than 8 mm, more preferably not more than 6 mm, especially preferably not more than 4 mm, for example not more than 3 mm. Preferably, when the burr guide assembly comprises a removable sheath, the diameter of the bore is larger than a burr guide assembly which does not include a removable sheath so as to accommodate the sheath without reducing the maximum diameter burr tool that can extend through the burr guide assembly.

The assembly will generally be made from metallic based materials which are conventionally used in the manufacture of surgical instruments. Certain stainless steels can be particularly preferred. However, it will be understood that at least one part of the assembly, for instance the drill guide block, can be made from polymeric materials. Using polymeric materials can reduce the cost of manufacture of the assembly, especially because an assembly made from polymeric materials can easily be manufactured using a moulding process. When the drill guide block is made from a polymeric material, it can be preferred that a removable drill guide sleeve that extends through a bore in the drill guide block is present, in order to protect the drill guide block from the drill bit extending through the bore. Suitable polymeric materials include certain polycarbonates, polyester, polyamides, poly-ether-ether ketones (PEEKs), and polyaryl-ether ketones (PAEKs). Polymeric materials can be reinforced with particulate material, especially fibrous materials, to provide appropriate wear characteristics.

Embodiments of the present invention will now be described by way of example only with reference to the accompanying drawings in which:

FIG. 6b is a perspective view of the assembly in which the guide sleeve shown in FIG. 3 is mounted in the second orientation.

FIG. 7 is a perspective view of the assembly in which the guide sleeve shown in FIG. 3 is mounted with a burr tool extending through it.

FIG. 9 is a perspective view of the assembly according to the second embodiment shown in FIG. 8 in isolation.

FIG. 10a is a side view of the assembly according to the second embodiment shown in FIG. 8.

FIG. 10b is a top view of the assembly according to the second embodiment shown in FIG. 8.

Figure 1:
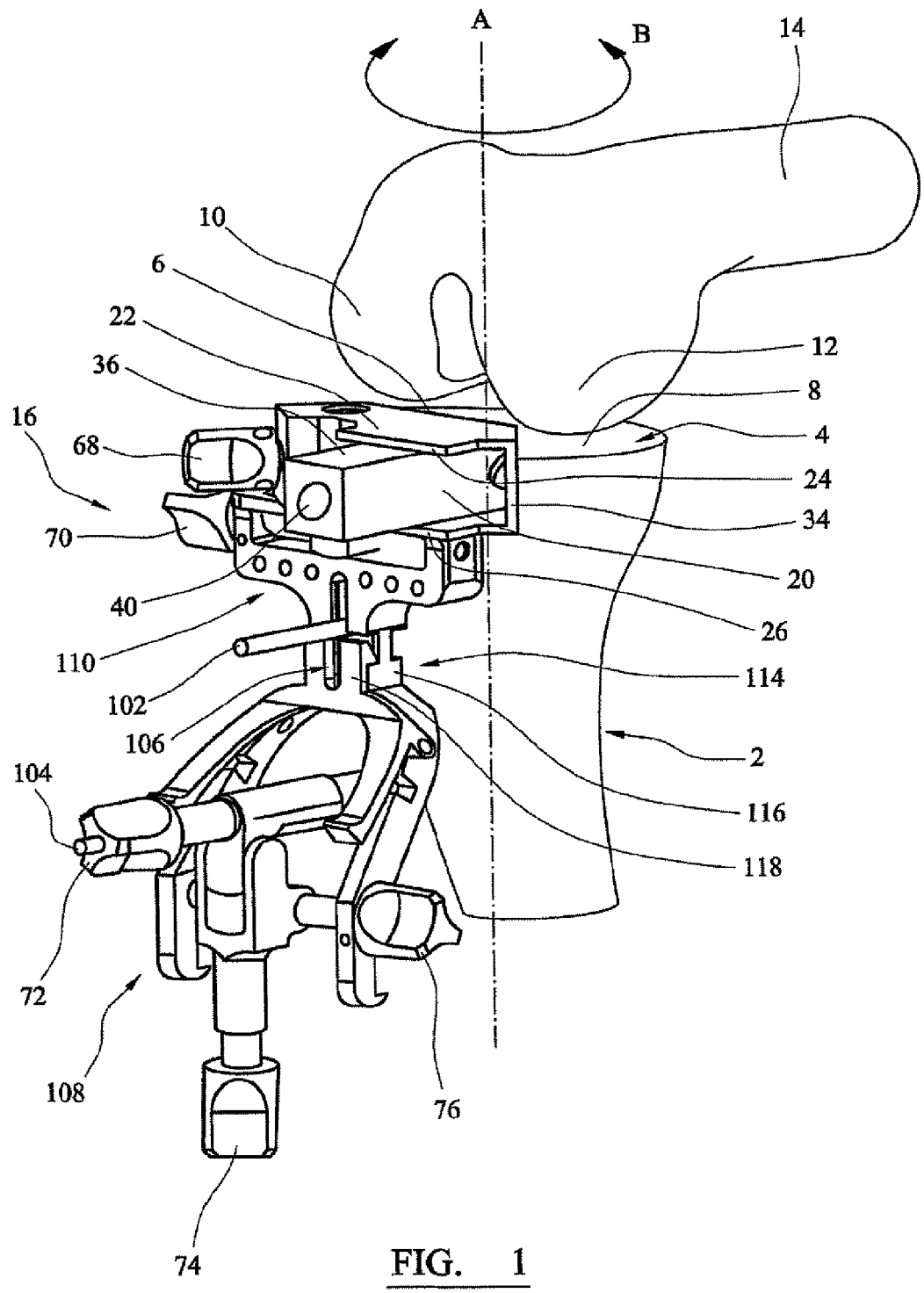
FIG. 1 is a perspective view of an assembly according to the present invention, mounted on the proximal tibia.

Referring to the drawings, FIG. 1 shows the proximal portion of a tibia 2, including the tibial plateau 4 of the tibia which has medial 8 and lateral 6 condyles for receiving the medial 12 and lateral 10 condyles of the distal part of a femur 14. The tibia 2 and femur 14 are shown in isolation to show how the present invention can be put into effect to prepare the tibia for implantation of a component of an orthopaedic joint prosthesis. The prosthesis can be used to provide a hard-wearing bearing surface on the proximal tibia 2, which can articulate with an appropriate prosthesis component which is implanted on the distal end of the femur 14. Although the invention is described in relation to preparing the proximal tibia, the present invention can be used to prepare planar surfaces on other bones, for example, the distal or proximal end of a femur, or the proximal or distal end of a humerus.

The preparation of the proximal tibia to receive a component of an orthopaedic joint prosthesis involves the formation of a planar surface on at least part of the proximal tibia, to receive a planar surface of the component.

FIG. 1 shows a burr guide assembly 16 according to the present invention fastened to the tibia 2. The burr guide assembly generally comprises a housing 110 which can be fastened indirectly to the tibia 2 by a jig 108, and a guide sleeve 20 which is pivotally mounted in the housing. The housing 110 provides a mounting 22 in which the guide sleeve 20 can be pivotally mounted.

The jig 108 has first 72, second 74 and third 76 adjustment screws which can be rotated to adjust the tibial slope, distal/proximal and varus/valgus positioning of the mounting 22 relative to the tibia, respectively. The housing 110 comprises a fourth 68 and fifth 70 adjustment screws which can be rotated to adjust and lock the internal/external rotational, and to adjust the medial/lateral position of the mounting 22 relative to the tibia, respectively.

The jig 108 can be fastened to the tibia 2 through the use of first 102 and second 104 fixing pins. The first fixing pin 102 extends through a channel 106 defined by the jig 108 and the housing 110. The channel 106 is elongated so as to allow the adjustment of the proximal/distal position of the housing 110 relative to the bone once the first fixing pin 102 has been fastened to the tibia 2. The first adjustment screw 72 is cannulated, and the second fixing pin 104 extends through first adjustment screw.

The jig 108 and housing 110 each define a portion of the channel 106 through which the first fixing pin 102 extends (i.e. the jig 108 and housing 110 each provide a V-shaped recess at their interface). The jig 108 and housing 110 can be releasably fastened to one another at their interfaces by a push release latch mechanism 114. However, it will be understood that other mechanisms other than a latch can be used to releasably fasten the housing 110 to the jig 108. The latch mechanism comprises a flap 116 provided on the housing 110 and a hook 118 provided on the jig 108. However, it will be understood that the flap can be provided on the jig 108 and the hook can be provided on the housing 110. When in the engaged position, a flat side of the flap 116 is held against a flat side of the hook 118 so as to prevent the jig 108 and housing 110 moving away from each other. The housing 110 can be released from the jig 108 by pulling the flap 116 away from the hook 118. It will be understood that the housing 110 and jig 108 need not be separate components (i.e. they can be one piece).

The jig 108 is a standard jig for receiving a surgical instrument, cutting block or tool so that its position can be accurately located and fixed, either directly or relative to the bone. Such jig instruments of this general kind are known, including those available from DePuy Products, Inc under the name CAS Preservation Tibial Jig (which is used as part of DePuy's MI TKR System surgical technique).

The mounting 22 of the housing 110 contains formations (not shown) which enable the guide sleeve 20 to be removably mounted within the mounting 22 so that it can pivot about the axis designated by A, in the direction illustrated by arrow B. The formation of the mounting 22 comprises two cylindrical projections (not shown) which are located on the inside of opposing parallel walls 24, 26 of the mounting 22 so that they are co-axial. Accordingly, the axis of the two cylindrical projections defines the axis A.

The mounting 22 further comprises two end walls extending between the two parallel walls 24, 26 at either end of the parallel walls. The end walls 34, 36 are angled so that when the assembly is in use the distance between the end walls decreases as you travel towards the tibia. Therefore, the cross-sectional shape of the mounting 22 when taken perpendicular to the axis A, generally the shape of an isosceles trapezoid. The end walls 34, 36 act as stops which limit the angle through which the guide sleeve 20 can pivot about axis A.

The parallel walls 24, 26 are separated by a distance that is slightly larger than the width of the guide sleeve 20 that is to be mounted between the walls. The distance is large enough such that the guide sleeve 20 is capable of easily sliding between the walls, but small enough such that any rotational force imparted on the sleeve when it is mounted is counteracted by the walls 24, 26 preventing the rotational movement of the sleeve.

Figure 2:
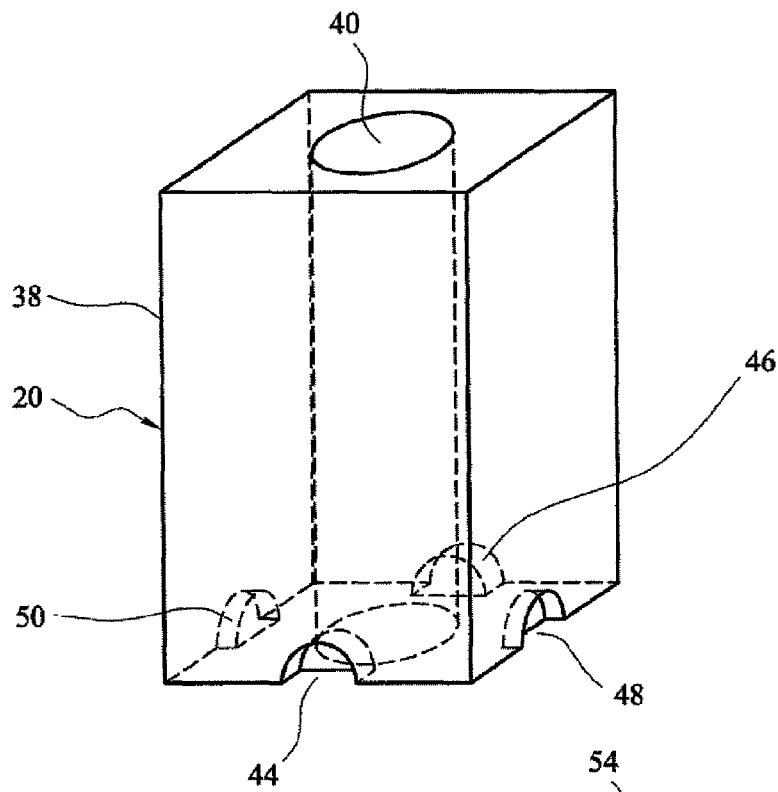
FIG. 2 is a perspective view of the guide sleeve of the assembly shown in FIG. 1, according to a first embodiment.

FIG. 2 shows the guide sleeve 20 in more detail. The guide sleeve 20 comprises a generally cuboidal sleeve 3 8 having a bore 40 that runs parallel to the axis of the cuboidal sleeve 38. Further, the cuboidal sleeve 38 and the bore 40 are co-axial. The diameter of the bore 40 is slightly bigger than the size of a burr tool (designated by reference numeral 42 shown in FIG. 7) which extends through the guide sleeve to cut the tibial plateau 4. The cuboidal sleeve 38 comprises first 44, second 46, third 48 and fourth 50 recesses for providing a bearing for the cylindrical projections (not shown) of the mounting 22. The first 44, second 46, third 48 and fourth 50 recesses are semi-circular in shape. The first 44 and second 46 recesses are located on opposite sides of the cuboidal sleeve, and the third 48 and fourth 50 recesses are located on the other two opposite sides of the cuboidal sleeve. The recesses are located at the end of the cuboidal sleeve 38 so that the recesses are open-ended. The use of open-ended recesses provided on each of the sides of the cuboidal sleeve 38 enables the guide sleeve 20 to be removably mounted into the mounting 22 in four different orientations.

Figure 3:
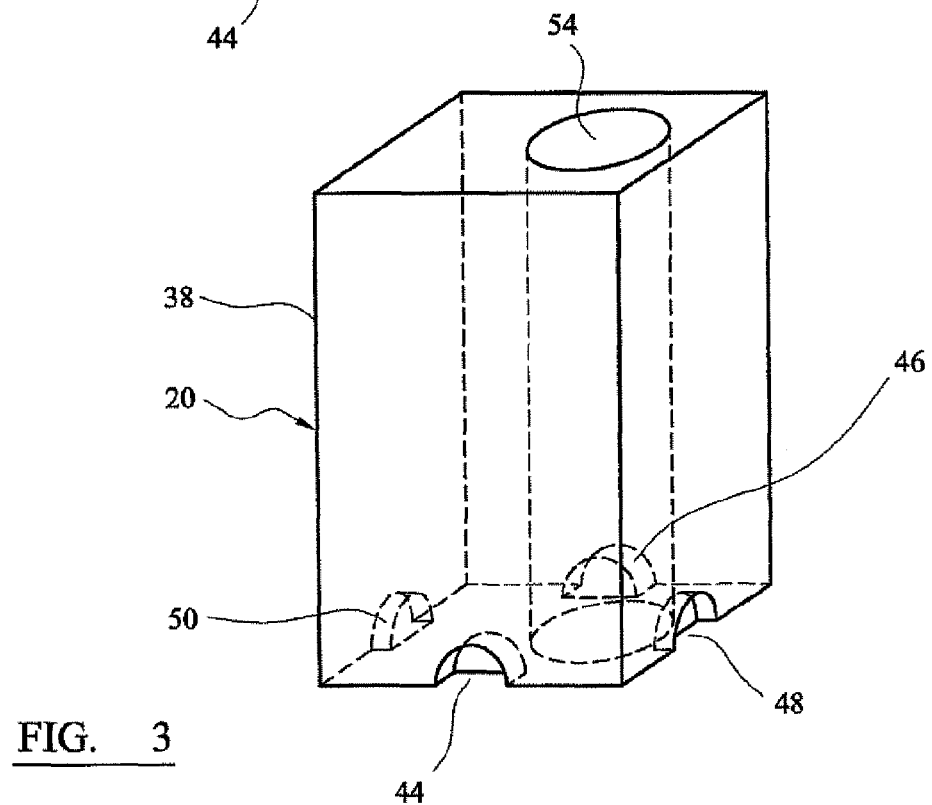
FIG. 3 is a perspective view of the guide sleeve of the assembly shown in FIG. 1, according to a second embodiment.

FIG. 3 shows a second embodiment of the guide sleeve 20 according to the present invention. The second embodiment of the guide sleeve is similar to that shown in FIG. 2, and like parts share like reference numerals, except that the bore 54 is located eccentrically within the cuboidal guide sleeve 38. The positioning of the bore 54 relative to the longitudinal axis of the cuboidal sleeve 38 is described in more detail with reference to FIG. 4a.

Figure 4A:
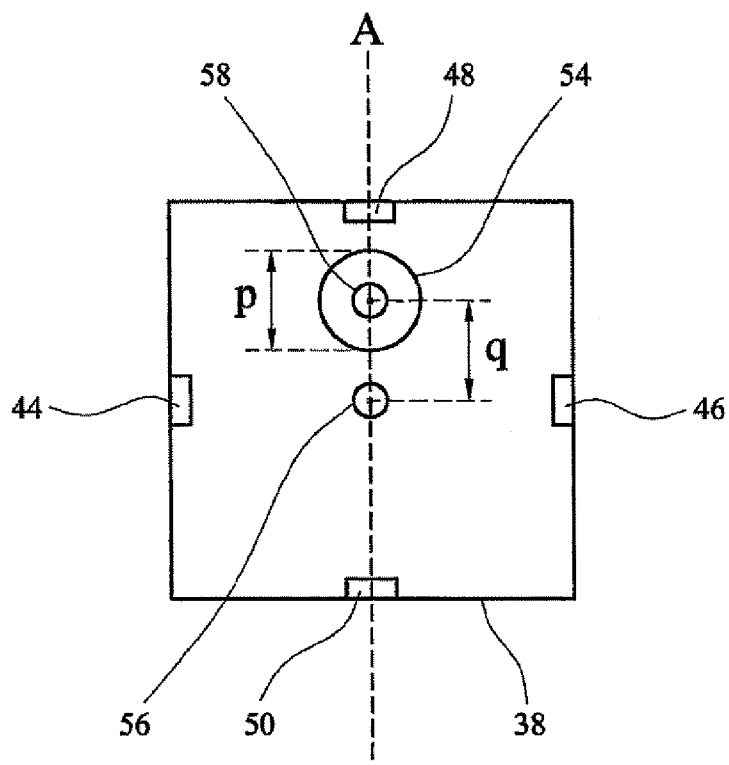
FIG. 4a is a bottom view of the guide sleeve shown in FIG. 3.
Figure 4B:
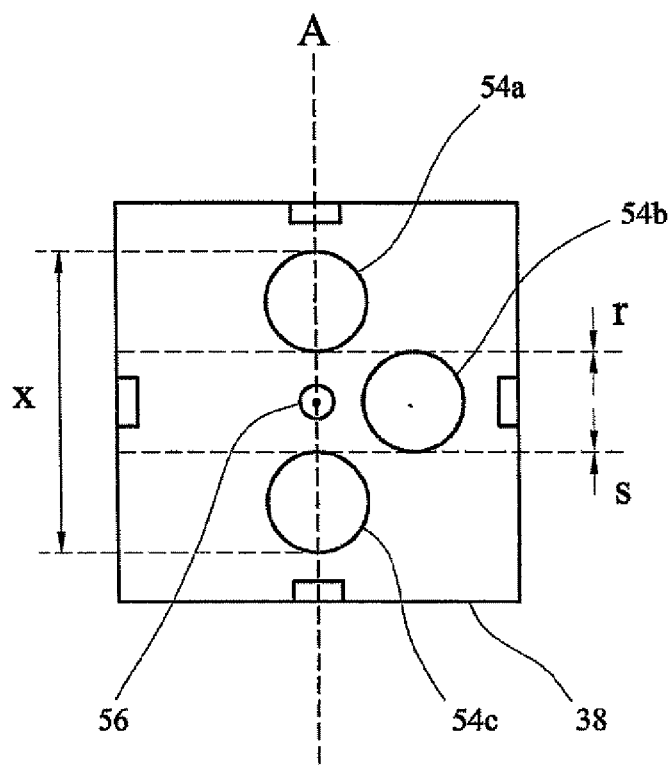
FIG. 4b is a bottom view of the guide sleeve shown in FIG. 3, illustrating the position of the bore when the guide sleeve is mounted in the housing in first, second and third orientations.

FIG. 4a shows the underside of the cuboidal sleeve 38 (i.e. the end of the cuboidal sleeve that will be close to the tibia during the cutting procedure). As shown in FIG. 4a, the bore 54 is located in the cuboidal sleeve 38 so that the centre point 58 of the bore 54 (i.e. its longitudinal axis) lies on the axis A about which the cuboidal sleeve 38 pivots. Further, the bore 54 is positioned so that the distance q between its centre point 58 and the centre point 56 of the cuboidal sleeve 38 (i.e. its longitudinal axis) is equal to the diameter p of the bore 54. As shown in FIG. 4a, the cuboidal 110 so that it pivots about the third 48 and fourth 50 recesses. (The mounting 22 is not shown in order to simplify the depiction of the cuboidal sleeve). As discussed above, the cuboidal sleeve 38 can be removed from the mounting and mounted in four different orientations. The relative positioning of the bore 54 in three of those orientations is described with reference to FIG. 4b. FIG. 4b shows the underside of the cuboidal sleeve 38. Bore 54a illustrates the positioning of the bore 54 when the cuboidal sleeve 38 is mounted in a first orientation. Bore 54b illustrates the position of the bore 54 when the cuboidal sleeve 38 is mounted in a second orientation. Bore 54c illustrates the position of the bore 54 when the cuboidal sleeve 38 is mounted in a third orientation.

In all orientations, the cuboidal sleeve is mounted in the mounting 22 so that it pivots about the same axis A. Therefore, in the first and third orientations, the cuboidal sleeve will pivot about the third 48 and fourth 50 recesses. In the second orientation, the cuboidal sleeve 38 will pivot about its first 44 and second 46 recesses. As illustrated, the distance, parallel to the axis A, between the edges of the bore 54 in its first orientation 54a and its second orientation 54b, indicated by distance r, is approximately zero. Further, the distance parallel to the axis A, between the edges of the bore 54 in its second orientation 54b and its third orientation 54c, indicated by distance s, is also approximately zero. Furthermore, the distance t that extends between the outermost edges of the bore 54 when the bore is in the first orientation 54a and the third orientation 54c is three times the size of the diameter p of the bore 54.

Figure 5A:
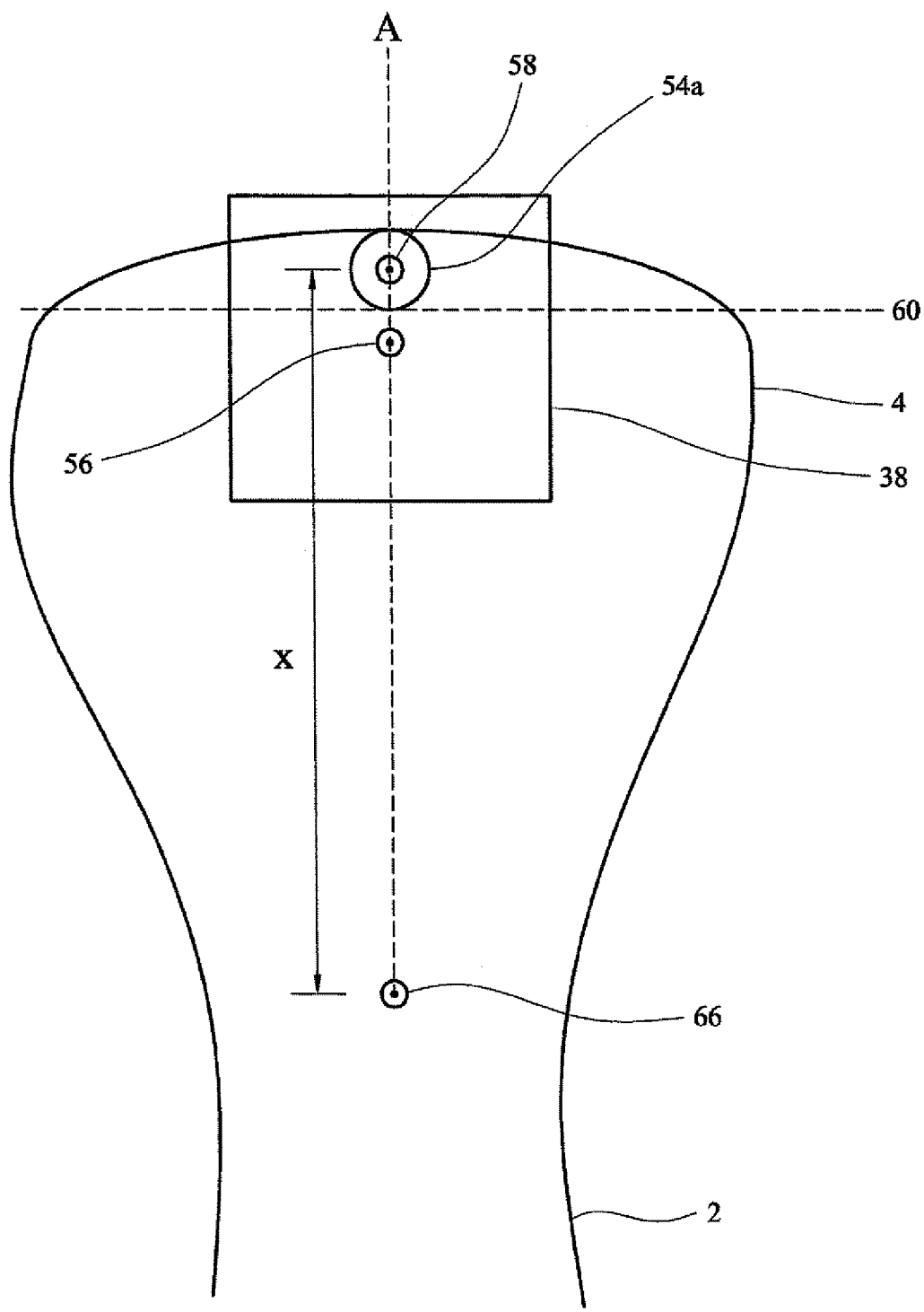
FIG. 5a is a schematic top view of the guide sleeve and the proximal tibia shown in FIG. 1 before a first cutting step.
Figure 5B:
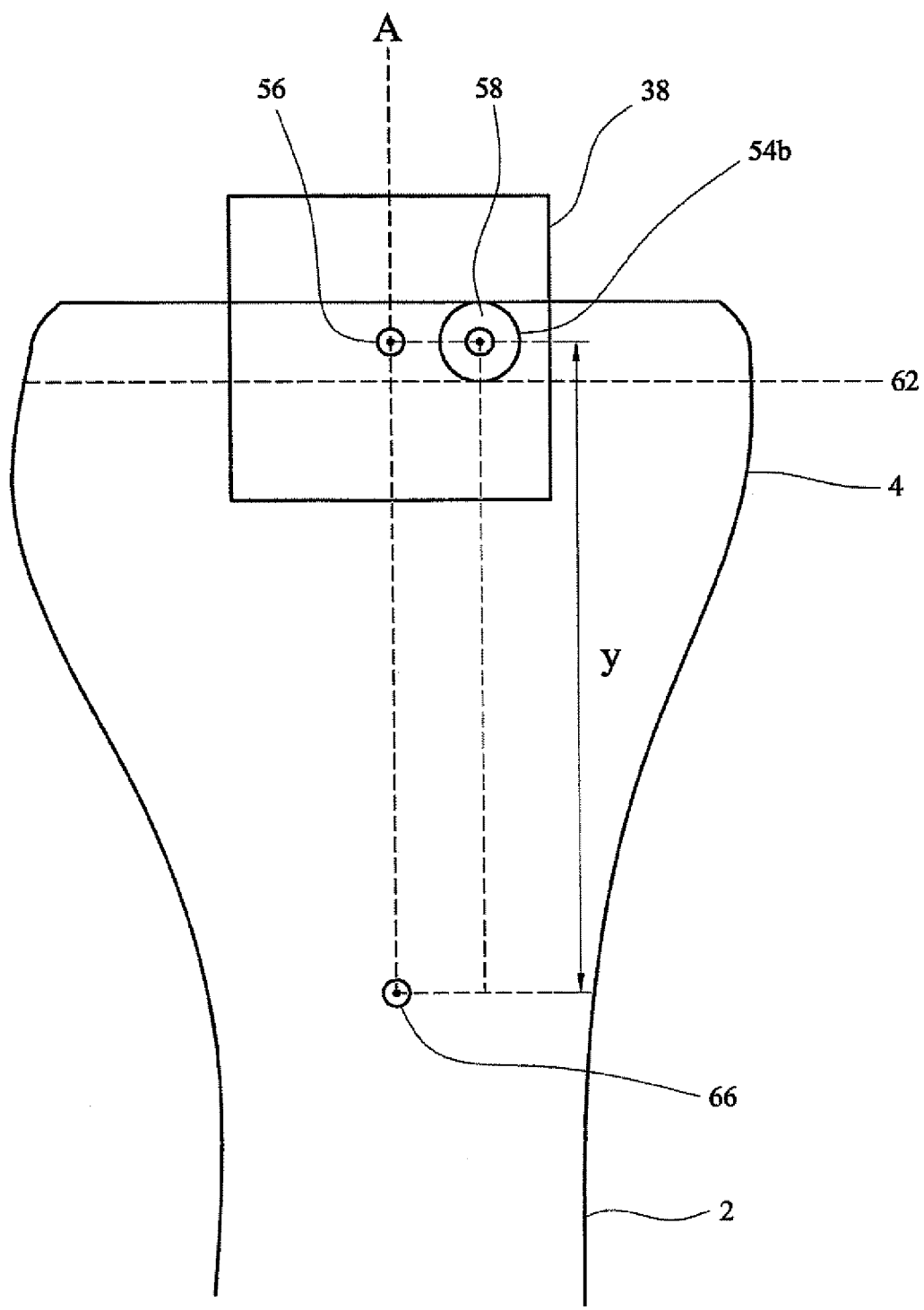
FIG. 5b is a schematic top view of the guide sleeve and the proximal tibia shown in FIG. 1 before a second cutting step.
Figure 5C:
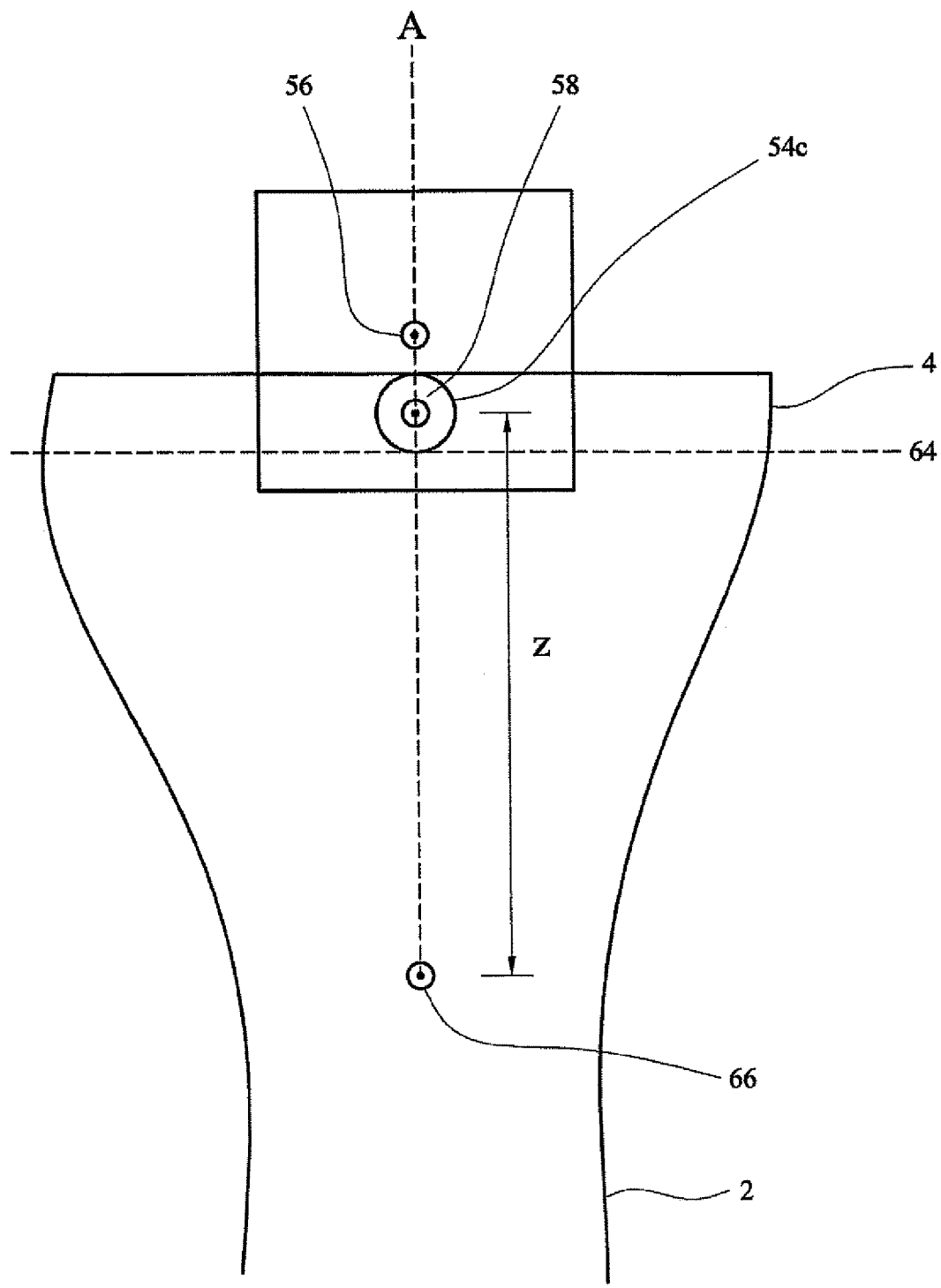
FIG. 5c is a schematic top view of the guide sleeve and the proximal tibia shown in FIG. 1 before a third cutting step.

FIGS. 5a, 5b and 5c show top views of the cuboidal sleeve 38 in situ, mounted relative to the tibia 2 before a first cutting step, a second cutting step and a third cutting step respectively is performed in order to prepare the tibial plateau 4. To simplify the illustration of the first, second and third cutting steps, the mounting 22, housing 110 and jig 108 of the assembly 16 is not shown. To perform a cutting step, the burr tool is inserted through the bore 54 so that the cutting part of the bore is close to the bone. The cuboidal sleeve 38 and burr tool are then pivoted about the axis A so until the cutting end of the burr tool is located on one side of the tibial plateau 4. The burr tool and cuboidal sleeve 38 are then pivoted about the axis A so that the burr tool sweeps through the tibial plateau in a plane guided by the cuboidal sleeve and in doing so, the burr tool removes a section of bone to leave a planar surface.

After each cutting step, the cuboidal sleeve 38 is removed from the mounting 22 in the housing, rotated by 90" about a centre point 56 of the cuboidal sleeve 38 and then remounted within the mounting 22. Although as illustrated in FIGS. 5a, 5b and 5c, the cuboidal sleeve 38 is rotated in a clockwise direction, the guide sleeve can be rotated in an anti-clockwise direction. The cuboidal sleeve 38 is mounted so that it pivots about axis A to each of its orientations. The intended cutting plane which is to be cut in the tibial plateau 4 by each of the first, second and third cutting steps is illustrated by lines 60, 62 and 64 respectively.

Distances x, y and z illustrate the distance between which the axis of the bore 54 intersects the axis A which extends perpendicularly to the intended cutting plane) and a point 66 in the bone which lies on axis A before the first, second and third cutting steps respectively. As illustrated, the distance y before the second cutting step is smaller than the distance x for the first cutting step. Further, the distance z before the third cutting step is less than the distance y before the second cutting step. Therefore, the bore 54 moves closer to the point 66 in the bone on each successive cutting step. Further, the amount by which the bore 54 moves closer to the point 66 is uniform for each cutting step (i.e. x−y=y−z).

Figure 6A:
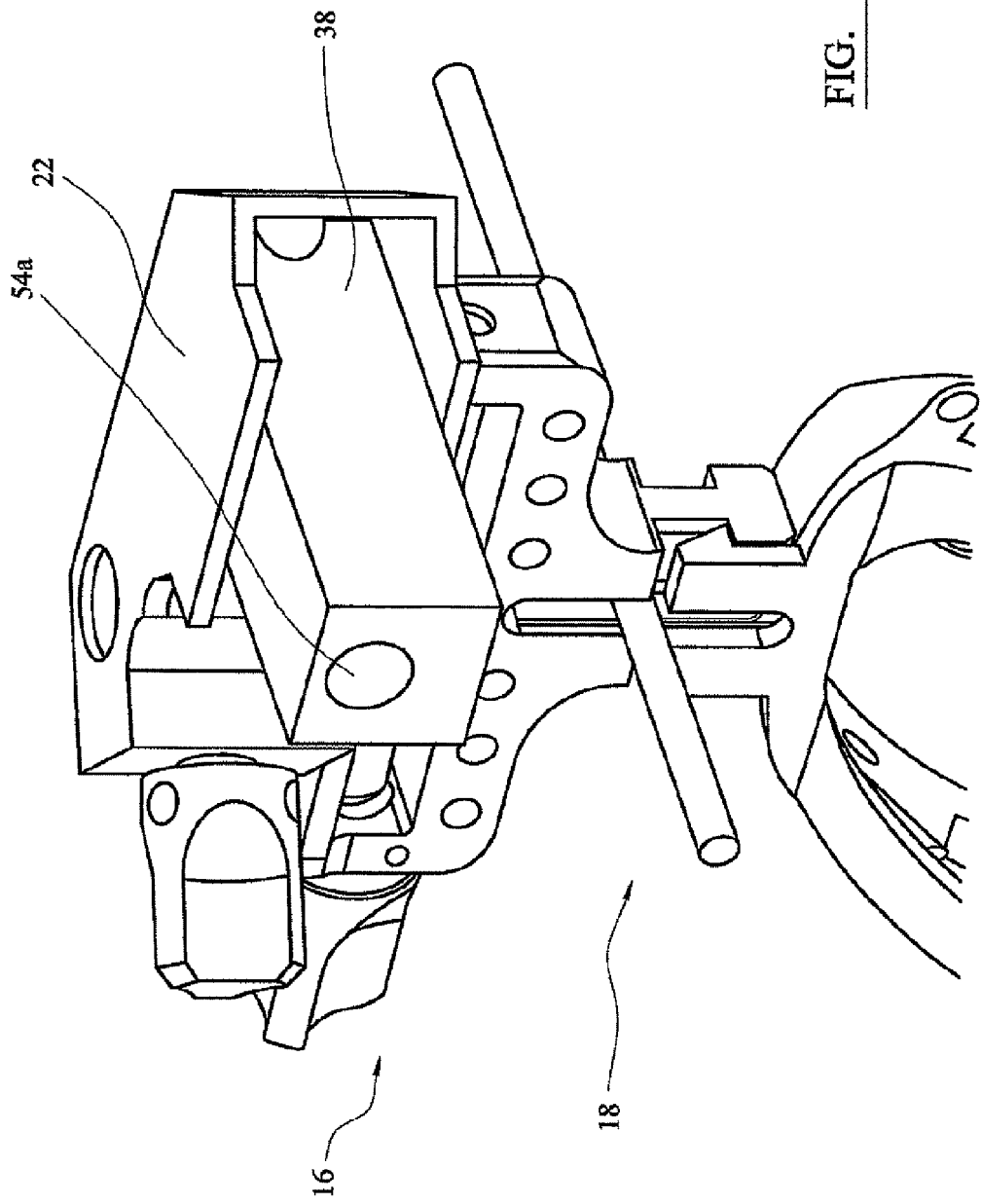
FIG. 6a is a perspective view of the assembly in which the guide sleeve shown in FIG. 3 is mounted in the first orientation.
Figure 6C:
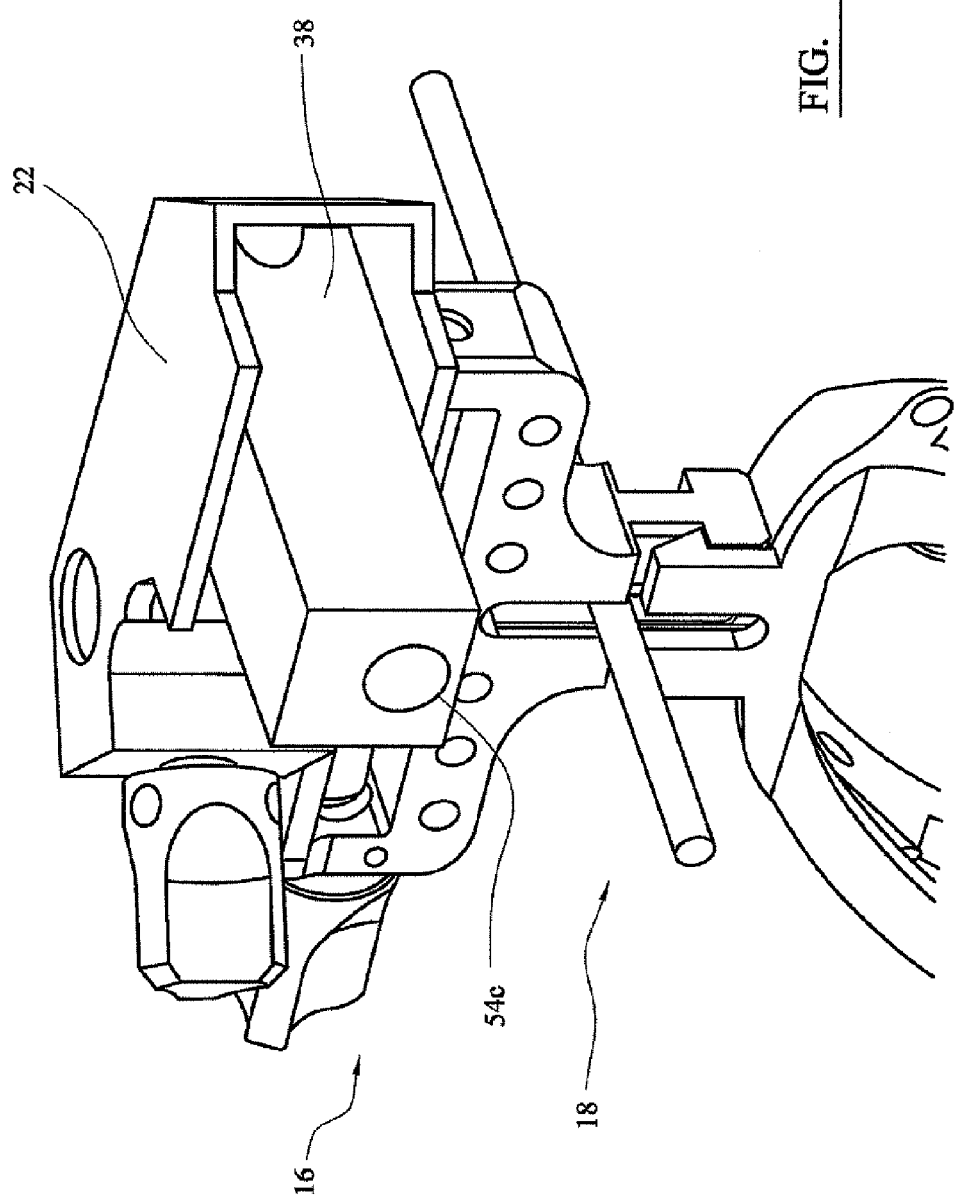
FIG. 6c is a perspective view of the assembly in which the guide sleeve shown in FIG. 3 is mounted in the third orientation.

FIGS. 6a, 6b and 6c show the cuboidal sleeve 38 being mounted within the mounting 22 of the housing 18 in its first orientation, second orientation and third orientation respectively before the first, second and third cutting steps respectively. The tibia 2 is not shown in FIG. 6a, 6b or 6c in order to simplify the illustration.

FIG. 7 shows the cuboidal guide sleeve 38 mounted in its third orientation, in which a burr tool 42 has been located in the guide sleeve 38. As illustrated, the guide sleeve 38 has been pivoted about its mounting around the axis A so that it has been displaced from its position shown in FIGS. 1, 6a, 6b and 6c.

Figure 8:
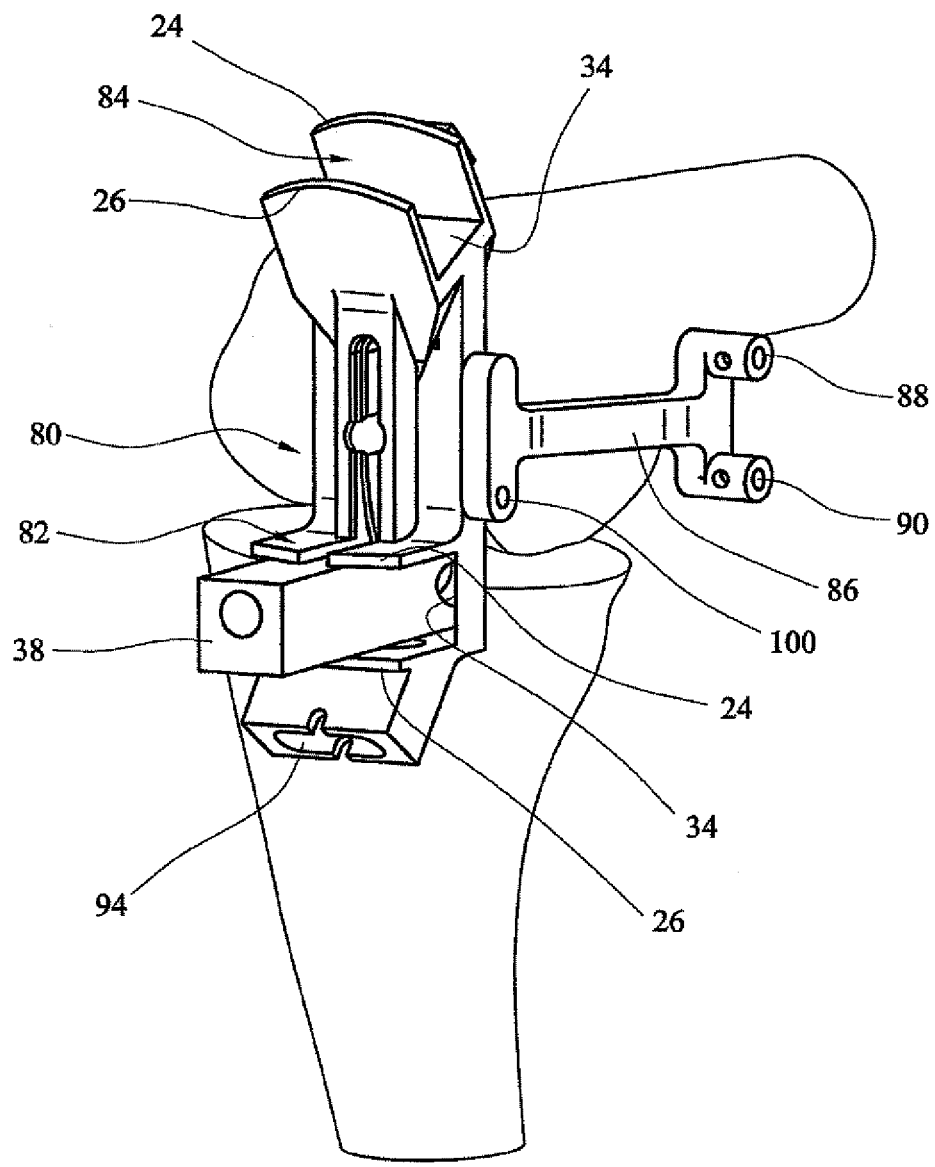
FIG. 8 is a perspective view of an assembly according to a second embodiment of the invention, mounted on the femur.

FIG. 8 shows a second embodiment of the housing 110 according to the present invention, for guiding a burr tool to perform a resection of the femur. The second embodiment of the housing 80 provides a first mounting 82 and a second mounting 84 in which the burr guide sleeve 38 can be removably mounted. The first and second mountings 82, 84 are similar to the mounting 22 of the housing 18, and like parts share like reference numerals. The first and second mountings 82, 84 comprise opposing parallel walls 24, 26 and first 34 and second (not shown) end walls extending between the parallel walls. The end walls 34 are angled so that when the assembly is in use the distance between the end walls decreases towards the bone. Also, there are formations (not shown) in the form of cylindrical projections on the inside of the parallel walls with which the recesses on the burr guide sleeve 38 can engage and pivot about. The first mounting 82 can be used to mount a guide sleeve 38 to guide a burr tool to resect the femur 14 on a first resection plane. The second mounting 84 can be used to mount a guide sleeve 38 to guide a burr tool to resect the femur 14 on a second resection plane.

The housing 80 can be fastened to the femur 14 by means of a bracket 86. The bracket 86 is fastened at a first end to the housing via means of a fixing pin (not shown) that extends through a first bore 100 in the bracket into the housing, and can be fastened to the bone at its second end by means of fixing pins (not shown) that extend through second and third bores 88, 90 in the bracket. In order to further secure the housing 80 to the femur 14, the housing 80 also provides a fourth bore 92 (see FIG. 10b) that extends through a block 98 located on the second mounting 84. The fourth bore 92 can receive a fixing pin (not shown) that can be inserted into the femur 14 to fasten the housing 80 to the femur.

The housing 80 also provides a slot 94 through which a burr tool or other surgical instrument can be inserted for providing a further resection or operation on the femur 14, for example, to resect the femur 14 on a third resection plane.

FIG. 9 shows a perspective view of the housing 80 in isolation. FIG. 10a shows the side view of the housing 80 and FIG. 10b shows the top view of the housing.

The use of a housing 80 that has two mountings 82, 84 can be advantageous when using a burr guide sleeve 38 to guide a burr tool (not shown) to resect a bone on two planes in successive steps. This is because the housing 80 can be used to provide suitable mountings for the burr guide sleeve 38 to guide a burr tool to perform such resections without the need to accurately locate and fasten the housing in two locations to perform the two resections. Instead, the housing 80 with two mountings 82, 84 can be located and fastened to the bone just once to provide two suitable mountings.

Although the second embodiment of the housing 80 is described in relation to removing bone material from/performing resections on a femur, it will be understood that this housing can also be fastened to and used for removing bone material from a tibia, or other bones, for example the humerus.

The invention claimed is:

1. A burr guide assembly for guiding a burr tool during a procedure in which the burr tool is used to cut a bone having a longitudinal axis, comprising:
   a housing configured to be attached to the bone;
   a guide sleeve attached to the housing such that, in use, the guide sleeve can freely pivot about a pivot axis within a defined range, the guide sleeve having a bore extending along its length, the bore being located eccentrically within the guide sleeve; and
   a burr tool having a cutting portion, the burr tool being configured to be at least partially disposed within the bore of the guide sleeve; wherein the guide sleeve is attached to the housing such that the cutting portion is substantially restricted to movement in a plane that is substantially perpendicular to the pivot axis.

2. The burr guide of claim 1, wherein the guide sleeve is removably attached to the housing.

3. The burr guide assembly of claim 2, wherein the sleeve has formations that enable the sleeve to be mounted within the housing in at least two orientations, the sleeve being pivotable about respective axes in each of the at least two orientations.

4. The burr guide assembly of claim 1, wherein the sleeve is cuboidal.

5. The burr guide assembly of claim 1, wherein the bore is sized so that the maximum transverse size of a burr tool that can be accommodated in the bore is 6 mm.

6. The burr guide assembly of claim 1, wherein the guide sleeve has a centerline and the distance between the center of the bore and the centerline is not more than about the radius of the bore.

7. The burr guide assembly of claim 1, wherein the housing comprises stops for limiting the angle through which the guide sleeve can pivot.

8. The burr guide assembly of claim 7, wherein the stops limit the angle through which the guide sleeve can pivot to not more than 90 degrees.

9. The burr guide assembly of claim 1, further comprising a drill guide block attachable to the housing, the drill guide block having an array of at least two spaced drill guide bores that define bone tissue which can be drilled by a drill bit extending through the bores towards the surface of the bone, wherein the ratio of the distance between the centers of two adjacent ones of the at least two bores to the diameter of each of those bores is not more than about 1.5.

10. The burr guide assembly of claim 1, wherein the pivot axis and the longitudinal axis are parallel when the housing is attached to the bone.

11. The burr guide assembly of claim 1, wherein the guide sleeve has a centerline, the bore has a bore axis and the bore axis is parallel to the centerline.

* * * * *